United States Patent
Sevenster et al.

(10) Patent No.: US 9,922,026 B2
(45) Date of Patent: Mar. 20, 2018

(54) SYSTEM AND METHOD FOR PROCESSING A NATURAL LANGUAGE TEXTUAL REPORT

(71) Applicant: KONINKLIJKE PHILIPS N.V., Eindhoven (NL)

(72) Inventors: Merlijn Sevenster, Chicago, IL (US); Yuechen Qian, Briarcliff Manor, NY (US); Johannes Buurman, 's-Hertogenbosch (NL)

(73) Assignee: Koninklijke Philips N.V., Eindhoven (NL)

(*) Notice: Subject to any disclaimer, the term of this patent is extended or adjusted under 35 U.S.C. 154(b) by 288 days.

(21) Appl. No.: 14/358,075

(22) PCT Filed: Oct. 24, 2012

(86) PCT No.: PCT/IB2012/055840
§ 371 (c)(1),
(2) Date: May 14, 2014

(87) PCT Pub. No.: WO2013/072795
PCT Pub. Date: May 23, 2013

(65) Prior Publication Data
US 2014/0316770 A1  Oct. 23, 2014

Related U.S. Application Data

(60) Provisional application No. 61/559,453, filed on Nov. 14, 2011.

(51) Int. Cl.
*G06F 17/28* (2006.01)
*G06F 17/21* (2006.01)
*G06F 19/00* (2018.01)

(52) U.S. Cl.
CPC .............. *G06F 17/28* (2013.01); *G06F 17/21* (2013.01); *G06F 19/3487* (2013.01)

(58) Field of Classification Search
None
See application file for complete search history.

(56) References Cited

U.S. PATENT DOCUMENTS 5,241,472 A   8/1993   Gur et al.
5,845,288 A   12/1998  Syeda-Mahmood
(Continued)

OTHER PUBLICATIONS

Lacoste, C. et al. "Medical Image retrieval based on knowledge assisted text and image indexing". IEEE Transactions on Circuits and Systems for Video Technology, vol. 17, No. 7, pp. 889-900, Jul. 2007.

(Continued)

Primary Examiner — Edwin S Leland, III

(57) ABSTRACT

A system for processing a report, comprising a natural language processing unit (1) for processing a natural language textual report to detect a description of a reference to at least part of a data object, wherein the description is expressed in natural language as a part of the natural language textual report. The system comprises an accessing unit (2) for accessing said at least part of the data object in a collection of data objects, based on the reference. The system comprises an associating unit (3) for associating the accessed at least part of the data object with the description of the reference. The natural language processing unit (1) comprises a view parameter extraction unit (4) for extracting a view parameter indicative of a view of the data object from the description of the reference.

13 Claims, 4 Drawing Sheets

(56) References Cited

U.S. PATENT DOCUMENTS

| | | | |
|---|---|---|---|
| 2003/0156745 A1* | 8/2003 | Saito | G06F 19/321 382/128 |
| 2006/0271403 A1* | 11/2006 | Iwasa et al. | 705/2 |
| 2010/0074481 A1* | 3/2010 | V | G06F 19/321 382/128 |
| 2011/0002515 A1* | 1/2011 | Futami | G06F 19/321 382/128 |
| 2011/0066635 A1* | 3/2011 | Moriya | G06F 19/3487 707/769 |
| 2011/0255754 A1* | 10/2011 | Dmitrieva | A61B 8/565 382/128 |
| 2012/0183188 A1* | 7/2012 | Moriya | 382/128 |
| 2013/0011027 A1* | 1/2013 | Zillner | G06F 19/3437 382/128 |
| 2013/0223708 A1* | 8/2013 | Fukatsu | G06K 9/6202 382/128 |
| 2014/0195266 A1* | 7/2014 | Mistry | G06Q 10/00 705/3 |
| 2014/0195267 A1* | 7/2014 | Mistry | G06Q 50/22 705/3 |
| 2014/0316770 A1* | 10/2014 | Sevenster | G06F 19/3487 704/9 |
| 2015/0235007 A1* | 8/2015 | Peters | G06F 19/3487 705/3 |
| 2015/0262014 A1* | 9/2015 | Iwamura | G06K 9/6253 382/128 |
| 2015/0324523 A1* | 11/2015 | Parthasarathy | G06F 19/322 705/2 |
| 2016/0071226 A1* | 3/2016 | Karale | G06Q 50/24 705/3 |
| 2016/0328517 A1* | 11/2016 | Deng | G06F 19/3487 |
| 2017/0024516 A1* | 1/2017 | Okabe | G06F 19/321 |
| 2017/0188816 A1* | 7/2017 | Ono | A61B 3/102 |

OTHER PUBLICATIONS

Allampalli-Nagaraj, G. et al. "Automatic semantic indexing of medical images using a web ontology language for case based image retrieval". Engineering Applications of Artificial Intelligence, 22, (2009), pp. 18-25.

Goldberg, D.W. et al. "From text to geographic coordinates: The current state of geocoding". URISA Journal, vol. 19, No. 1 (2007) p. 33-46.

Ahern, S. et al. "World Explorer: Visualizing aggregate data from unstructured text in geo-referenced collections". Proceedings of the 7th ACM/IEEE—CS joint conference on Digital libraries, pp. 1-10, ACM, NY (2007).

* cited by examiner

SYSTEM AND METHOD FOR PROCESSING A NATURAL LANGUAGE TEXTUAL REPORT

This application is a national stage application under 35 U.S.C. § 371 of International Application No. PCT/IB2012/055840 filed on Oct. 24, 2012 and published in the English language on May 23, 2013 as International Publication No. WO/2013/072795, which claims priority to U.S. Application No. 61/559,453 filed on Nov. 14, 2011, the entire disclosures of which are incorporated herein by reference.

FIELD OF THE INVENTION

The invention relates to processing a report.

BACKGROUND OF THE INVENTION

A number of application domains make use of text documents in their work process. For example, radiologists routinely review medical images and document their work in the form of free-text reports. Although these reports may have a number of standardized sections, the content of the sections contains natural language. Frequently, radiologists incorporate explicit references to image data in their reports. When reading the report, it may take time and/or effort to look up the referenced image data.

"Medical-Image Retrieval Based on Knowledge-Assisted Text and Image Indexing", by C. Lacoste et al., in IEEE Transactions on Circuits and Systems for Video Technology, Vol. 17, No. 7, pp. 889-900, July 2007, discloses to facilitate automatic indexing and retrieval of large medical-image databases. Both images and associated texts are indexed using medical concepts from the Unified Medical Language System (UMLS) meta-thesaurus.

"Automatic semantic indexing of medical images using a web ontology language for case-based image retrieval", by G. Allampalli-Nagaraj et al., in Engineering Applications of Artificial Intelligence 22 (2009) pp. 18-25, discloses a system implemented to evaluate the retrieval efficiency of images when they are semantically indexed using a combination of a web ontology language and the low-level features of the image.

SUMMARY OF THE INVENTION

It would be advantageous to have an improved way of processing a report. To better address this concern, a first aspect of the invention provides a system comprising:
a reference description detector for processing a natural language textual report to detect a description of a reference to at least part of a data object, wherein the description is expressed in natural language as a part of the natural language textual report; and
an associating unit for associating the at least part of the data object with the description of the reference.

The use of natural language processing to detect the description of a reference, and the associating unit for associating at least part of a data object corresponding to the description of the reference, makes it possible to use the textual report as if it were a structured dataset similar to a data record in a computer program or in a database. Such a data record can contain pointers to other data records, which pointers may be used in software engineering. Using the system described above, it becomes feasible to use a textual report that was entered by a radiologist in natural language as if it were such a structured dataset. This allows to look up all the relevant data objects necessary for understanding the report at hand automatically. The associating unit associates at least part of an existing data object that is related to a specific expression in the text report. This functionality makes it easy to create new applications that combine the report with the relevant data object in a meaningful way.

The system may comprise an accessing unit for accessing said at least part of the data object in a collection of data objects, based on the reference. This way, the at least part of the data object can be easily obtained when accessing the description of the reference. For example, a link or a hyperlink can be created. Such a link can be clicked on within a report viewer, for example, to pop up the associated at least part of the data object.

The system may comprise a description interpreter for interpreting the detected description of the reference, to obtain a normalized representation of the reference. By converting the natural-language description of the reference into a normalized representation, other modules in the system can use the reference without needing natural language processing capabilities.

The description interpreter may comprise a view parameter extraction unit for extracting a view parameter indicative of a view of the external data object from the description of the reference. This allows identifying the referenced part of the data object more precisely based on a view parameter, because the view parameter may relate to a particular portion of the object. Alternatively, the view parameter may describe a viewing mode of the at least part of the object. Such a viewing mode may include maximum projection imaging, or perspective view, for example.

The data object may comprise an image dataset. The view parameter may be indicative of a coordinate value relating to the image dataset. Such a system allows to find the correct views for a report, and more particularly for a particular phrase in a report, without having to store a snapshot of the view with the report. Instead, the view may be automatically re-created based on the textual description itself. Alternatively, the system may be used to automatically attach, for example, a snapshot of the view to the report.

The coordinate value may relate to a slice number of the image dataset. This is a common example of a coordinate value, and it is useful to recognize slice numbers and find the appropriate slice in the correct image dataset automatically.

The system may comprise a view generator for generating a view of the data object based on the view parameter. This is convenient for re-creating the referenced view of the data.

The data object may comprise an image dataset. The description interpreter may comprise an object description extraction unit for extracting a description of an object that is graphically represented by the image dataset. This allows to handle references to objects that are shown in the image dataset.

The accessing unit may comprise an object detector for detecting the object in the image dataset based on the description of the reference. This allows to identify the part of the image dataset corresponding to the reference.

The system may comprise a view generator for generating a view of the data object. The view generator may be arranged for emphasizing the object that was detected in the image dataset. This allows to indicate to a user the referenced object in the image dataset by emphasizing the object.

The system may comprise a user input handler for enabling a user to select the description of the reference in the text report. The system may also comprise a view generator for generating a view of said at least part of the object based on the association in response to an activation of the reference user input. This provides an easy way for a user to view images that correspond to a written text.

The system may comprise a view generator for generating a view of a data object based on a view parameter. The system may further comprise a reference indicator for indicating that the generated view corresponds to the description of the reference, based on the association. For example, the system provides an indication of the description of the reference within the view of the report, by means of e.g. an arrow pointing to the description of the reference or by means of highlighting the description of the reference. The system may further comprise a user input to enable a user to select the view to be generated by the view generator.

The system may be implemented partly or completely in a workstation.

In another aspect, the invention provides a method of processing a report, comprising processing a natural language textual report to detect a description of a reference to at least part of a data object, wherein the description is expressed in natural language as a part of the natural language textual report; and generating an association between the description of the reference and said at least part of the data object.

In another aspect, the invention provides a computer program product comprising instructions for causing a processor system to perform the method set forth.

It will be appreciated by those skilled in the art that two or more of the above-mentioned embodiments, implementations, and/or aspects of the invention may be combined in any way deemed useful.

Modifications and variations of the image acquisition apparatus, the workstation, the system, the method, and/or the computer program product, which correspond to the described modifications and variations of the system, can be carried out by a person skilled in the art on the basis of the present description.

It will also be appreciated that the image data may comprise two-dimensional, three-dimensional or higher-dimensional image data. The image data may be the product of an x-ray scanner, ultrasound, magnetic resonance imaging, computed tomography, nuclear medicine, or any other imaging modality.

BRIEF DESCRIPTION OF THE DRAWINGS

These and other aspects of the invention are apparent from and will be elucidated with reference to the embodiments described hereinafter. In the drawings, similar items are indicated by the same numerals.

DETAILED DESCRIPTION OF EMBODIMENTS

Figure 1:
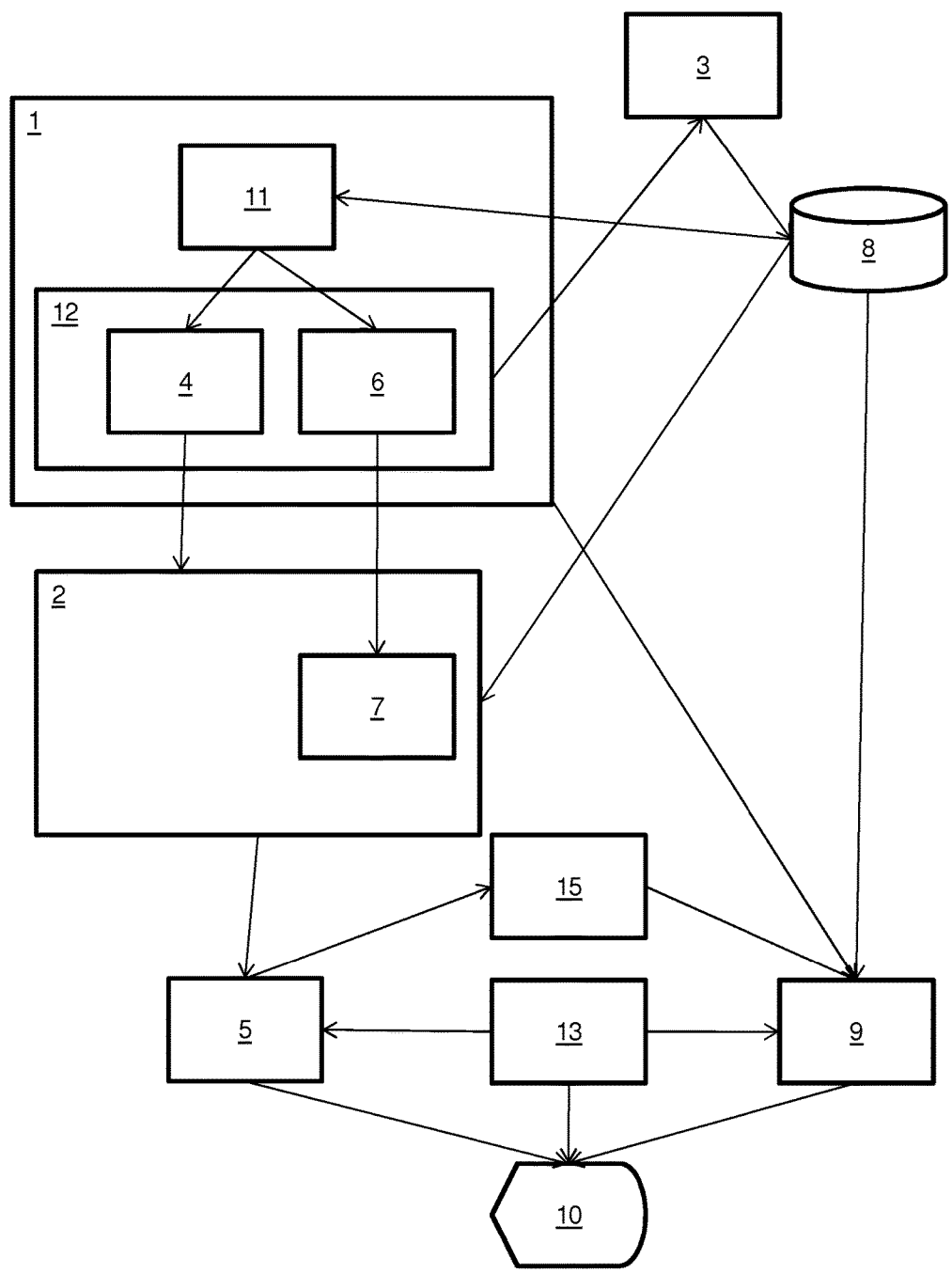
FIG. 1 is a diagram of a system for processing a report.

FIG. 1 shows a block diagram of a system for processing a report. The system may be implemented by means of a processor loaded with suitable software. For example, the system may be part of, or interact with, a database system 8 comprising a collection of reports and associated data objects. The database system 8 may be, for example, a healthcare information system. The system for processing a report may be part of a viewing workstation, for example. The system may thus be arranged for processing the reports that are viewed on the viewing workstation. At least part of the system may also be implemented as a pre-processing unit, that processes the reports, and stores the result of the processing in the database system 8. A viewing station may, thereafter, make use of the processing result. Such a processing result, as will be described hereinafter, may include an association between a phrase in the report and at least part of a data object stored in the database system 8. In addition, view parameters applicable to said at least part of a data object may be stored and used by the viewing station.

The system may comprise a report selector (not shown) for selecting a report from the database system 8, based on a user input or a user's task list. The report selector may retrieve the report from the database system 8 and forward it to a natural language processing unit 1. The skilled person will understand that the report may be obtained in another way, for example by enabling a user to type or dictate the contents of the report.

The system may comprise a natural language processing unit 1 for processing the natural language textual report. The natural language text report may comprise an electronic document that represents a text. The text report may contain a description or other information relating to data objects stored in the database system 8, or data objects that are otherwise made available. Moreover, the text report may contain a reference in natural language to such a data object or to a particular portion of such a data object. The natural language processing unit 1 may comprise a reference description detector 11 arranged to detect such a description of a reference to at least part of a data object. This description may be expressed in natural language as a part of the natural language textual report. Techniques to detect and process such a reference expressed in a natural language document are available to the person skilled in the art. For example, a rule-based system or a regular expression may be used for this purpose. The natural language processing unit 1 may comprise a description interpreter 12 arranged for interpreting the detected description of the reference, to obtain a normalized representation of the reference. This interpretation may be performed by using techniques in the art of natural language processing. The normalized representation may comprise, for example, a representation in XML format or another standardized format.

The system may comprise an accessing unit 2 for accessing said at least part of the data object. For example, the accessing unit 2 sends a query based on the normalized representation of the reference to the database system 8 to identify the data object in a collection of data objects stored in the database. The accessing unit 2 may be arranged for converting the standardized representation into a suitable query that is accepted by the database system 8. Alternatively, the standardized representation of the reference is suitable as a query to the database system 8, and the accessing unit 2 can forward the standardized representation, possibly wrapped in a suitable data wrapper, to the database system 8.

The system may further comprise an associating unit 3 for associating the referenced at least part of the data object with the description of the reference in the report. For example, the associating unit 3 may create a hyperlink in the report that provides an explicit link from the text passage describing the reference to the actual database object. Alternatively, the associating unit 3 may store the association between the report and the at least part of the database object in the database. Other kinds of associations are also possible. For example, the association may be displayed to a user, without storing the association in the database.

The natural language processing unit 1 may comprise a view parameter extraction unit 4 for extracting a view parameter indicative of a view of the data object from the description of the reference. For example, all kinds of viewing modes can be described in the report. These viewing modes include slice view, perspective view, shaded surface view, direct volume rendering, maximum intensity projection. Each of these view modes have parameters associated therewith, such as slice number, level/width setting, point of view, viewing angles, and more. These parameters may also be described in the report and extracted from the report by the view parameter extraction unit 4. In case the data object is not an image dataset, appropriate parameters may apply. For example, an ECG may have as parameters a time window or a lead label.

The data object may comprise an image dataset, and the view parameter may be indicative of a coordinate value relating to the image dataset. Such a coordinate value can be the slice number in case of slice view, or a point of view and/or a viewing direction in case of a perspective view, for example.

The system may comprise a view generator 5 for generating a view of said at least part of the data object based on the view parameter. For example, after extracting the indication of the image dataset and slice number from the report by the natural language processing unit 1, the accessing unit may access the image dataset and the view generator may generate a view according to the extracted view parameter.

The natural language processing unit 1 may comprise an object description extraction unit 6 for extracting a description of an object that is graphically represented by the image dataset. For example, a term describing a particular organ or pathology may be described. From the context, the natural language processing unit 1 may determine that the reference to the data object specifically refers to this object. In such a case, the normalized representation of the reference may include a normalized representation of that object.

The accessing unit 2 may comprise an object detector 7 for detecting the object in the image dataset based on the description of the object. To this end, the accessing unit 2 may be arranged for receiving an object dataset that represents the object. The object detector 7 may thereafter apply an object detection technique, known in the art per se, to detect the described object, based on the normalized representation of the reference.

The view generator 5 may be arranged for emphasizing the object that was detected in the image dataset. For example, the object may be segmented, or displayed in a different color or otherwise indicated to the user. Also, the displayed slice may be adapted to a slice that shows the referenced object, even if the description does not include a specific slice number.

The view generator 5 may be operatively connected to a display device 10, that is used to display the generated view of the object dataset. Moreover, a text report display unit 9 may be provided that causes the report to be displayed on the display device 10. The view generator 5 and the text report display unit 9 may be arranged for displaying the report and the associated views at the same time. Also, or alternatively, the text report display unit 9 may be arranged for indicating the detected descriptions of references in the displayed report text, for example by underlining or color coding. Moreover, a user input handler 13 may be provided, that is arranged for handling user input events received from a user input device (not shown), such as a mouse. The user input handler 13 may be arranged for enabling a user to select a detected description of a reference in the report. For example, the selecting takes place by pointing to the description of the reference using a mouse pointer or by using cursor keys or by touching the description on a touch sensitive display device. Alternatively, the references may be presented in a list, and the user may be enabled to select one of the references may be from that list. In response to the selection of a reference, the view generator 5 may be triggered by the user input handler 13 to generate and display the corresponding view on the display device 10.

The user input handler 13 may, additionally or alternatively, be arranged to receive an indication of a particular view to be generated by the view generator 5. The view generator 5 may also receive signals from other modules in the system (not shown), to generate a particular view of a particular part of a data object. A reference indicator 15 may be operatively coupled to the view generator 5 and the display unit 9 to cause the display unit 9 to provide an indication of any description of a reference that is associated with the currently generated view. This indicating may be realized by highlighting or by drawing a symbol next to the description, for example. Alternative means of indication are also possible, for example by reading out loud the related passage using speech technology.

At least some of the functionality described may be made accessible via a workstation. The computations and processing steps performed by the different units of the system may be performed on the workstation itself or on a server remote of the workstation.

Figure 2:
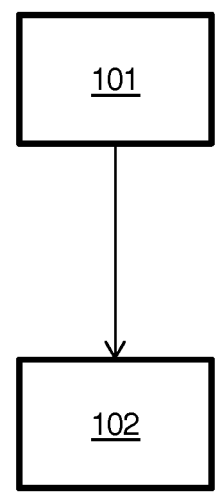
FIG. 2 is a flow chart illustrating aspects of a method of processing a report.

FIG. 2 illustrates a method of processing a report. The method comprises step 101 of processing a natural language textual report to detect a description of a reference to at least part of a data object, wherein the description is expressed in natural language as a part of the natural language textual report. The method further comprises step 102 of identifying said at least part of the data object in a collection of data objects, based on the description of the reference. The method may be extended or modified by applying processing steps explained above with reference to the system. The method and the system may be implemented at least partly in a computer program.

It may be useful to create a hyperlink from textual references to the data objects containing the images themselves. This would help radiologists in their workflow: when reading the report of a previous case, having access to key pictures through hyperlinks in the report, makes it easier for the radiologists to access the previous images. This holds in particular for MR and CT image, as they are typically large in size and are volumetric data sets. This makes finding the observation discussed in the report time consuming.

Moreover, non-radiology clinicians may find such hyperlinked images useful. Another reason why this functionality is useful for other clinicians is that they may not be familiar with the radiologist's information system, or the radiologist's style of reporting image coordinates. It would thus be helpful if a system could assist them to get easy access to their patients' key cases.

Any one or more of the following modules may be present in a system for processing textual reports containing textual references to one or more images.

A pattern extraction module may be provided that parses the content of a report and recognizes textual references to image coordinates. Such a pattern extraction module can be implemented based on regular expressions. Alternative embodiments of a pattern extraction module include statistical and rule-based approaches. As an example, if the report contains a sentences "A punctuate area of abnormal signal is seen in the right cortical spinal tract in the anterior medulla.

This is best seen on image five and six of series 4", a pattern extraction module used with the present invention may recognize the phrase "image five and six of series 4".

A normalization module may be provided that maps the recognized image coordinates in the report to an internal object representing a (list of) image coordinate(s). Each image coordinate may have an image identifier and a series identifier, among other information. The phrases that are extracted by the pattern extraction module may be first mapped to a list of controlled values. The list of controlled values may include terms like "image" and "series" and also digits. The individual words in the recognized phrases are mapped to the controlled values, taking into account any morphological variations, and transferring numerals to the corresponding digit representations. With reference to the above example, in this manner, the phrase "image five and six of series 4" may be mapped to the following list of controlled values: [image, 5, 6, series, 4]. Such a list may be mapped to a (list of) image coordinates using, for example, sequential reasoning rules. These reasoning rules may make use of contextual information, such as previously extracted image coordinates, etc. In the above-referenced example, the exemplary list [image, 5, 6, series, 4] may be transformed into the list of objects: (image:5, series:4) and (image:6, series:4).

A context analyzer may be provided that maps the normalized image information to DICOM attributes. This applies to the case where the data objects are associated with DICOM attributes. In alternative systems, appropriate attributes of the referenced data objects are mapped to. In the case of medical image reporting, a report is typically associated with an imaging study that contains a plurality of imaging series. In some clinical workflows, one report can be associated with a plurality of imaging studies. A context analyzer may assign an image series identifier to an extracted image coordinate. This may be done, for example, using one or a combination of the follow methods.

On the image viewing workstation, series are typically lined up one next to another. By using the series index in the image coordinate, the context analyzer can look up the corresponding series and extract relevant DICOM attributes to query the PACS system. Such DICOM attributes may include StudyInstanceUID, SeriesInstanceUID, PatientName, PatientID, StudyID. The set of DICOM attributes that is used depends on the PACS that services the query and this set can be customized for different institutes.

Alternatively or additionally, the context analyzer can extract image series information from the text surrounding a description of an image coordinate. For example, regular expressions may be used to process this surrounding information. For example, consider the following text passage in a report: "A new focal supratentorial white matter lesion is seen adjacent to the Lateral ventricle on the right side. It measures approximately 8 mm×7 mm in size and is best seen on series 6 image 21. Associated low T1 signal is seen in the lesion but no definite enhancement is present." In this example, the text "series 6 image 21" may be converted into the image coordinates (image:6, series:4) by the above-described modules. Moreover, the context analyzer may determine that the image coordinates (image:6, series:4) referenced in the report is associated with a T1 series, based on the phrase "Associated low T1 signal" in the subsequent sentence. Again, regular expressions can be used to detect for example terms such as "T1", "T2", "MR", and "US".

An interface to a PACS system may be provided that retrieves a pointer to image data, given an image coordinate object and its context DICOM information. The system may use the DICOM attributes to query the PACS system. The PACS system may have an API that allows retrieving image data on the basis of these DICOM attributes.

A user interface module may be provided that presents to the user the textual image reference, the normalized image coordinates, and/or the image data retrieved. An image viewing environment can be embedded in user interface components, such as a tool tip or pop-up controls. Alternatively, the system may extract all images and present them to the user as he or she loads the reports. This will give the user the feeling of reading a graphically enriched report.

Figure 3:
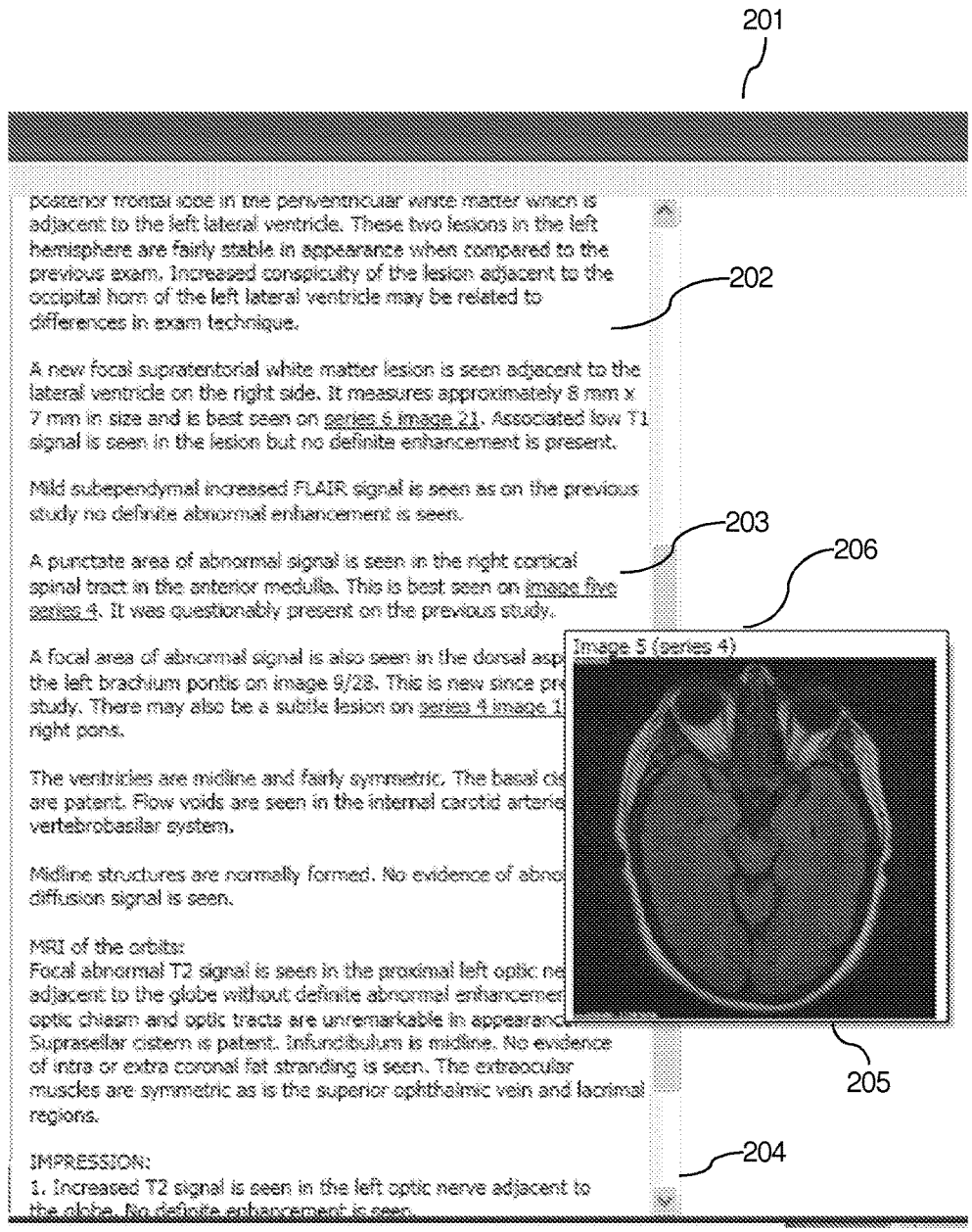
FIG. 3 is an example of a screenshot of the system in use.

FIG. 3 shows a screenshot of an application comprising the system for processing a report. The figure shows a window 201 generated by the application. The window 201 displays a part of a report in a text frame 202. The user may scroll through the report by means of a scrollbar 204. In the report, several portions of text are underlined. For example, at 203, the text "image five series 4" is underlined. This is an example of a way to indicate to the user that this is a recognized textual description of a reference to a data object. These recognized textual references may be hyperlinked to the corresponding data object views. When the user hovers the mouse over one of the hyperlinks, or otherwise indicates a recognized textual reference, a preview 205 of the referenced view of the data object may be displayed. Also, the standardized image coordinates 206 may be displayed as a confirmation to the user that the image correctly matches the description.

It is also possible that the system enables a user, such as a radiologist, to select a view, for example image 5 of series 4, in the window 205. When the user navigates to image 5, the system may automatically highlight the sentence with the corresponding text passage 203. Doing so allows the user to find the portions of the textual report that describe or otherwise relate to that view.

Figure 4:
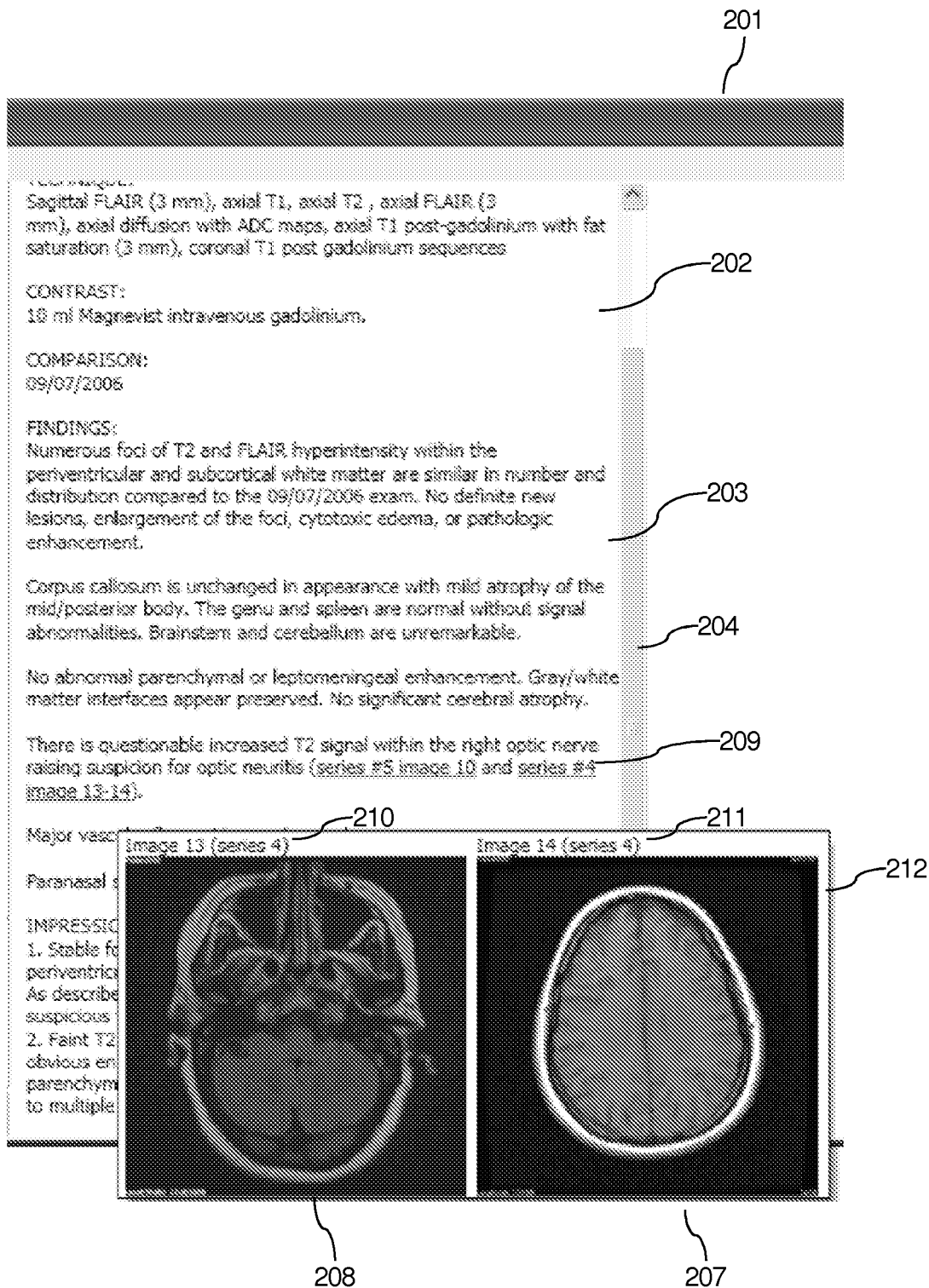
FIG. 4 is another example of a screenshot of the system in use.

Note that if a phrase refers to two or more images, this may be handled by the system by displaying all the images simultaneously or sequentially, or by enabling the user to select one or more of the referenced images for viewing. Alternative methods to handle multiple images may also be implemented. FIG. 4 is another screenshot that may be produced by the same or another embodiment of the application. The screenshot of FIG. 4 illustrates the situation that a single reference references a plurality of image views. The same reference numerals are reproduced in FIG. 4 to refer to similar objects as in FIG. 3. The description thereof is omitted here. In the example of FIG. 4, the report contains a description "series #4 image 13-14" at numeral 209. This description refers to a range of images, including image 13 and image 14. When the user indicates this description 209, the view generator 5 pops up a window 212 with both referenced images. Image 13 of series 4 is displayed at 208 and is identified by standardized coordinates 210, whereas image 14 of series 4 is displayed at 207 and is identified by standardized coordinates 211.

The system may also be arranged for indicating in the report any phrases that are recognized as a textual image reference, but could not be resolved to a complete image reference, for example because some information, such as the series coordinates, is missing.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for processing a report, comprising a reference description detector for processing a natural language textual report to detect a description of a reference to at least part of a data object, wherein the description is expressed in natural language as a part of the natural language textual report;
an associating unit for generating an association between the description of the reference and said at least part of the data object; and
a description interpreter for interpreting the detected description of the reference, to obtain a normalized representation of the reference,
wherein the description interpreter comprises a view parameter extraction unit for extracting a view parameter indicative of a view of the data object from the description of the reference.

2. The system according to claim 1, further comprising an accessing unit for accessing said at least part of the data object in a collection of data objects, based on the reference.

3. The system according to claim 1, wherein the data object comprises an image dataset, and wherein the view parameter is indicative of a coordinate value relating to the image dataset.

4. The system according to claim 3, wherein the coordinate value relates to a slice number of the image dataset.

5. The system according to claim 1, further comprising a view generator for generating a view of said at least part of the data object based on the view parameter.

6. The system according to claim 1, wherein the data object comprises an image dataset, and wherein the description interpreter comprises an object description extraction unit for extracting a description of an object that is graphically represented by the image dataset.

7. The system according to claim 6, wherein the accessing unit comprises an object detector for detecting the object in the image dataset based on the description of the object.

8. The system according to claim 7, further comprising a view generator for generating a view of the data object, and wherein the view generator is arranged for emphasizing the object that was detected in the image dataset.

9. The system according to claim 1, further comprising
a user input handler for enabling a user to select the description of the reference in the text report; and
a view generator for generating a view of said at least part of the object based on the association in response to an activation of the reference user input.

10. The system according to claim 1, further comprising
a view generator for generating a view of a data object based on a view parameter; and
a reference indicator for indicating that the generated view corresponds to the description of the reference, based on the association.

11. A workstation comprising a system according to claim 1.

12. A method of processing a report, comprising
processing a natural language textual report to detect a description of a reference to at least part of a data object, wherein the description is expressed in natural language as a part of the natural language textual report;
generating an association between the description of the reference and said at least part of the data object;
interpreting the detected description of the reference, to obtain a normalized representation of the reference; and
extracting a view parameter indicative of a view of the data object from the description of the reference.

13. A computer program product to be loaded by a computer arrangement, comprising instructions for processing a natural language textual report, the computer arrangement comprising a processing unit and a non-transitory memory, the computer program product, after being loaded, providing said processing unit with the capability to carry out the tasks of:

detecting a description of a reference to at least part of a data object, wherein the description is expressed in natural language as part of the natural language textual report;

associating said at least part of the data object in a collection of data objects, based on the reference;

interpreting the detected description of the reference, to obtain a normalized representation of the reference;

extracting a view parameter indicative of a view of the data object from the description of the reference;

enabling a user to select the description of the reference in the text report; and generating a view of said at least part of the object based on the association in response to an activation of the reference user input.

* * * * *